United States Patent [19]

Sun

[11] 4,052,466

[45] Oct. 4, 1977

[54] PROCESS FOR THE PREPARATION OF BISPHENOL-A

[75] Inventor: Kwok K. Sun, Hamden, Conn.

[73] Assignee: The Upjohn Company, Kalamazoo, Mich.

[21] Appl. No.: 726,835

[22] Filed: Sept. 27, 1976

[51] Int. Cl.$^2$ .................. C07C 37/20; C07C 37/00; C07C 39/16
[52] U.S. Cl. ...................... 260/619 A; 260/345.5
[58] Field of Search ...................... 260/619 A

[56] References Cited

U.S. PATENT DOCUMENTS

| 2,433,143 | 12/1947 | Mohrman | 260/619 A |
| 2,480,533 | 8/1949 | Winnek | 260/619 A |
| 2,540,633 | 2/1951 | Rourk | 260/619 A |

*Primary Examiner*—Norman Morgenstern
*Attorney, Agent, or Firm*—Denis A. Firth; John Kekich

[57] ABSTRACT

The use of certain dihydric phenols, alkyl ethers thereof, and alkyl-substituted monohydric phenols, as promoters in the acid catalyzed condensation of phenol and acetone to form Bisphenol-A enables said reaction to be carried out more rapidly, at significantly lower temperatures in some instances, with greater selectivity, i.e. reduction in proportion of undesired by-product, and most significantly, with the use of only catalytic amounts of mineral acid (instead of the large quantity in the conventional process) or the use of the inexpensive solid catalysts, such as acidic clays, which due to their low catalytic ability, are not useful as sole catalyst for this condensation if the promoter is not present. The promoters are readily recoverable for re-use.

25 Claims, No Drawings

PROCESS FOR THE PREPARATION OF BISPHENOL-A

BACKGROUND OF THE INVENTION

1. Field of the Invention

This invention relates to processes for the preparation of bisphenols and is more particularly concerned with an improved process for the preparation of Bisphenol A by the condensation of phenol and acetone.

2. Description of the Prior Art

The condensation of phenol with acetone to produce Bisphenol A [2,2-di(p-hydroxyphenyl)propane] is a reaction well-known in the art. A variety of catalysts has been suggested for use in this reaction. Such catalysts include hydrogen chloride (see, for example, U.S. Pat. Nos. 2,182,308 and 2,191,831), boron trifluoride (Chemical Abstracts 58, 3338c), perchloric acid (Chemical Abstracts 60, 1626h), benzenesulfonic acid (Chemical Abstracts 59, 511h), and various cation exchange resins (see, for example, British Pat. Nos. 842,209; 849,965 and 883,391). The use of various thiol compounds, in combination with one or other of the above catalysts, has been reported. Illustratively, U.S. Pat. No. 2,468,982 shows the use of thioglycolic and 3-mercaptopropionic acids and esters thereof as catalysts and U.S. Pat. No. 2,623,908 shows the use of combinations of such mercaptoalkanoic acids and hydrochloric acid. The use of thiophenols (U.S. Pat. No. 2,359,242), combinations of hydrochloric acid and alkylmercaptans (U.S. Pat. No. 2,775,620) and hydrogen sulfide (Chemical Abstracts 58, 1403e) has also been reported.

We have now found that the use of certain phenols and ethers thereof as promoters, in combination with known catalyst systems for the condensation of phenol and acetone, gives rise to significant improvements in the overall results achieved in said condensation.

SUMMARY OF THE INVENTION

This invention comprises an improved process for the preparation of Bisphenol A by condensing phenol and acetone in the presence of acidic catalysts wherein the improvement comprises employing as cocatalyst a member selected from the group consisting of compounds of the formulae:

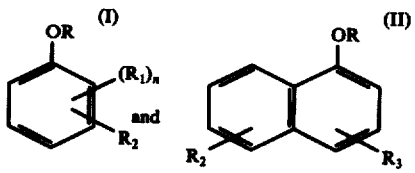

wherein R and $R_2$ are independently selected from the class consisting of hydrogen and lower-alkyl, $R_1$ is selected from the class consisting of hydroxyl, lower-alkoxy and lower-alkyl, $n$ is an integer from 1 to 2, and $R_3$ is selected from the class consisting of hydrogen, hydroxyl, lower-alkoxy and lower-alkyl.

The term "lower-alkyl", as used throughout the specification and claims, means alkyl from 1 to 6 carbon atoms, inclusive, such as methyl, ethyl, propyl, butyl, pentyl, hexyl, and isomeric forms thereof. The term "lower-alkoxy", as used throughout the specification and claims, means alkoxy from 1 to 6 carbon atoms, inclusive, such as methoxy, ethoxy, propoxy, butoxy, pentyloxy, hexyloxy, and isomeric forms thereof.

DETAILED DESCRIPTION OF THE INVENTION

The condensation of phenol and acetone to form Bisphenol A in accordance with the invention is carried out using the procedures conventional in the art for this process with the principal exception that the cocatalyst (I) or (II) is incorporated into the initial reaction mixture.

Thus, the phenol and acetone are brought together in the presence of the catalyst at a temperature which is within the range of about 40° to about 100° C. The reaction temperature employed in any given instance is generally dependent upon the nature of the acidic catalyst employed as will be discussed in more detail below.

The phenol and acetone are generally employed in at least stoichiometric proportions, i.e. at least two (2) moles of phenol per mole of acetone but advantageously the phenol is employed in excess of this proportion and in amounts up to about 20 moles per mole of acetone. The use of excess phenol in this manner tends to reduce the amount of undesirable by-products, i.e. the trimer and higher oligomers, which are produced in the reaction.

The acidic catalyst which is employed in combination with the cocatalyst (I) or (II) in accordance with the invention can be any of the acid catalysts hitherto known and used to catalyze the condensation. Such acidic catalysts include mineral acids such as hydrogen chloride (in anhydrous form or in the form of the concentrated aqueous acid), Lewis acids such as boron trifluoride (generally employed as the etherate to facilitate handling), zeolites, ion-exchange resins such as polystyrene polysulfonic acids. There can also be employed acidic catalysts which were not known and used previously for this condensation such as acid clays.

By "acid clay" is meant a clay which, when suspended in water (10 – 15% w/v), exhibits a pH less than 7.0. The clays meeting these requirements include those which are acid in the natural state in which they are found as well as those which can be derived by washing a naturally occurring clay with a mineral acid in order to adjust the pH to any predetermined level. Such clays, i.e. those which are acidic in the natural state as well as those which can be rendered acid by washing in the above manner, are a well-recognized class of naturally occurring hydrated alumina silicates. Illustrative of the clays which, if necessary after acid washing, can be employed in the process of the invention are: montmorillonitic clays including fuller's earth, bentonites, montmorillonite and the like, attapulgus clays, kaolins, bauxite, and the like. A wide variety of such clays is available commercially. For example, kaolin clays in various particle sizes are available from the J. M. Huber Corporation, Huber, Ga. Bentonite clays in a variety of grades are available under the trade name Filtrol from the Filtrol Corporation, Los Angeles, Calif. Montmorillonitic clays are available under the trade name Impact from the Milwhite Company, Houston, Tex. and under the trade name KSF from Chemetron Corporation.

Preferably the calcined acid clays are employed in powder form in the catalyst combination used in the process of the invention. A number of the above exemplified clays are available in pelletized form but the use of such forms, while within the scope of the present invention, is less preferred than the use of powders.

The natural and synthetic zeolites which are employed as the acidic component of the cocatalyst combinations in the process of the invention, are also a well-recognized class of materials. The synthetic zeolites are described, for example, by R. W. Grimshaw, The the Chemistry and Physics of Clays, Fourth Edition Revised, 1971, pp. 168-9, Ernest Benn Limited, London, and D. W. Breck, Zeolite Molecular Sieves, John Wiley and Sons, New York. The zeolites are hydrated aluminosilicates having a relatively open crystal lattice which can be readily synthesized and which can be subjected to cation exchange to produce forms having different cations. For use in the process of the invention the zeolites are converted to the hydrogen form. The naturally occurring zeolites are inclusive of sodium and calcium aluminosilicates such as faujisite, anocite, chabazite, heulandite, notrolite, stilbite and thomsonite; see, for example, Encyclopedia of Chemical Technology, Vol. 12, p. 295, 1954, Interscience Publishers Inc., New York, N.Y. A particularly useful group of zeolites for use in the process of the present invention are the decationized zeolites known as Types X and Y in the hydrogen form.

Other types of ion-exchange resin which can be employed as the acidic component of the cocatalyst combination used in the process of the invention include polystyrene polysulfonic acids such as that available under the trade name Amberlyst (Rohm & Haas Co., Philadelphia, Pa.) and styrene divinylbenzene copolymers available under the trade name Dowex (Allied Chemical Co.).

The acidic components of the cocatalyst systems of the invention are employed in amounts within the range of about 5 parts by weight to about 50 parts by weight per 100 parts by weight of phenol employed in the condensation.

The compounds of formulae (I) and (II) which are employed as cocatalyst with the aforesaid acidic catalysts in the process of the invention are employed in a proportion within the range of about 0.1 to about 10 moles percent, and preferably within the range of about 0.5 to about 2.0 moles percent, based on phenol employed in the reaction. The various compounds represented by the formulae (I) and (II) are all well-known in the art. Representative of said compounds are catechol, resorcinol, hydroquinone and the mono- and di-methyl and the mono- and di-ethyl ethers thereof, p-ethylphenol, o-cresol, p-cresol, orcinol (3,5-dihydroxytoluene) and the mono- and di-lower alkyl ethers thereof, pyrogallol (1,2,3-trihydroxybenzene) and the mono-, di- and tri-lower-alkyl ethers thereof, phloroglucinol (1,3,5-trihydroxybenzene) and the mono-, di- and tri-lower-alkyl ethers thereof, thymol (2-isopropyl-5-methylphenol), α-naphthol, 5-methyl-α-naphthol, 6-isobutyl-α-naphthol, 1,4-dihydroxynaphthalene, 6-hexyl-1,4-dihydroxynaphthalene, 6-methyl-4-methoxy-α-naphthol, and the like.

In carrying out the condensation of phenol and acetone in accordance with the invention the various reactants and catalysts are brought together, in any order, and the reaction mixture is heated, advantageously with agitation, at a temperature within the range set forth above. It is found that acidic catalysts such as hydrochloric acid or boron trifluoride generally require temperatures in the lower end of the range while somewhat higher temperatures are employed when the acid catalyst is an acid clay or ion-exchange resin. The most appropriate range of reaction temperature for any given catalyst combination can be determined readily by small scale test runs.

The progress of the condensation can be followed using routine analytical procedures such as infrared spectroscopy, nuclear magnetic resonance spectroscopy and the like carried out on aliquots of the reaction mixture. When the reaction is adjudged to have attained a desired extent of conversion, using such analytical techniques, the desired product, namely, the Bisphenol A is isolated from the reaction mixture by procedures well-known in the art. Thus, the catalyst in the reaction mixture is removed either by filtration in the case of solid catalysts or by neutralization with a base in the case of using a catalytic amount of acid as catalyst. The neutral, catalyst-free, reaction mixture is distilled under reduced pressure to remove the excess phenol and the unconverted acetone leaving the Bisphenol A as residue. The latter can be purified, if desired, by fractional crystallization or other conventional techniques.

The mixture of phenol and the unreacted acetone recovered in the above distillation can be used as such, without separation, as starting material in a subsequent condensation of phenol and acetone in accordance with the invention.

In an alternative to the above described procedures, the Bisphenol-A can be recovered from the reaction product as follows. After the catalyst is removed from the reaction mixture Bisphenol A is isolated as a complex with phenol by crystallization from the neutral molten mixture. Bisphenol A of high purity can be obtained by heating the crystalline complex under reduced pressure to remove the complexing phenol by distillation at temperatures up to 160° C at 0.1 mm. of mercury. The mother liquor of the crystallization comprises a mixture of excess phenol, the unconverted ketone, and the compound of formula (I) or (II) used as cocatalyst. This mixture can be recycled as such without separation and used as starting material in the subsequent condensation.

The use of compound (I) or (II) as cocatalyst with the acidic catalyst produces a number of significant improvements in the overall result achieved in the condensation of the phenol and acetone. Firstly, the condensation can be carried out in the presence of only catalytic amount of acid or of inexpensive acidic clays as catalyst. Without the use of (I) and (II) the reaction requires the presence of a large quantity of the acid and the catalytic ability of the clays is too low to be applicable. Secondly, the rate of reaction is markedly increased so that the condensation can be carried out at lower temperature. This is a significant factor on a commercial scale of operation since reduction in reaction time and temperature produces a saving in energy consumption, labor costs and increases throughput in a given piece of chemical equipment. Thirdly, selectivity of the reaction is improved, i.e. the proportion of undesirable by-products [chiefly 2,2,4-trimethyl-4(4'-hydroxyphenyl) chroman and oligomers] is reduced, as compared with a condensation in which the acidic catalyst is employed alone without the presence of the compound (I) or (II) as cocatalyst.

In a further embodiment of the invention it has been found that incorporation into the catalyst system of the instant process of any of the thiols or sulfides previously employed as cocatalysts with acids in the condensation of phenol and acetone, will enhance still further the increase in rate of reaction effected by using the combination of acidic catalyst and the compound of the formula (I) or (II). A preferred thiol is thioglycolic acid.

The amount of thiol or sulfide employed in this embodiment is advantageously within the range of about 0.01 mole percent to about 10 mole percent per mole of phenol and is preferably in the range of about 0.1 mole percent to about 2 mole percent, per mole of phenol.

The following examples describe the manner and process of making and using the invention and set forth the best mode contemplated by the inventors of carrying out the invention but are not to be construed as limiting.

EXAMPLE 1

A mixture of 47.0 g. (500 mmol.) of phenol, 2.9 g. (50 mmol.) of acetone, 0.55 g. (5 mmol.) of resorcinol and 0.12 g. (1.25 mmol.) of concentrated aqueous hydrochloric acid was stirred and heated at 75° C for 3.5 hours. The reaction mixture was neutralized by aqueous sodium carbonate solution, washed to neutral with deionized water and dried over anhydrous magnesium sulfate. The dried solution was filtered, and the filtrate was distilled under reduced pressure (0.1 mm. of mercury) at 50° up to 160° C to remove excess phenol and resorcinol. The residue solidified to a white crystalline solid [5.62 g.; 49.3 percent conversion based on phenol consumed] which was found by high pressure liquid chromatography to contain 94.4 percent by weight of Bisphenol A (94.1 percent by weight 4,4'-isomer; 5.9 percent by weight 2,4'-isomer), 2.3 percent by weight of oligomers and 3.2 percent by weight of an unidentified compound.

EXAMPLE 2

The process of Example 1 was repeated exactly as described except that 0.23 g. (2.5 mmol.) of thioglycolic acid was added to the initial reaction mixture and the amount of concentrated aqueous hydrochloric acid was increased to 0.258 g. (2.5 mmol.). There was obtained, as the residue after removal of excess phenol, unconverted acetone and resorcinol, 10.1 g. (78.6 percent conversion based on phenol consumed) of crude Bisphenol A which was found by high pressure liquid chromatography to contain 98.4 percent by weight of Bisphenol A (93.9 percent 4,4'-isomer: 6.1 percent 2,4'-isomer) and 1.6 percent by weight of oligomers.

EXAMPLE 3

The process of Example 1 was repeated exactly as described except that 0.23 g. (2.5 mmol.) of thioglycolic acid was added to the initial reaction mixture and the concentrated hydrochloric acid was replaced by 0.355 g. (2.50 mmol.) of freshly distilled boron trifluoride etherate. The reaction was carried out in an atmosphere of nitrogen. There was obtained, as the residue after removal of excess phenol, acetone and resorcinol, 10.12 g. (88.7 percent conversion based on phenol consumed) of crude Bisphenol A which was found by high pressure liquid chromatography to contain 97.9 percent by weight of Bisphenol A (93.7 percent 4,4'-isomer; 6.3 percent 2,4'-isomer), 0.2 percent by weight of 4-(p-hydroxyphenyl)-2,2,4-trimethylchroman and 1.9 percent by weight of oligomers.

EXAMPLE 4

A mixture of 47.0 g. (500 mmol.) of phenol, 2.9 g. (50 mmol.) of acetone, 0.55 g. (5 mmol.) of resorcinol, 0.23 g. (2.5 mmol.) of thioglycolic acid and 12.5 g. of KSF (acid-treated montmorillonite clay: pH = 2: Chemetron Corp.) was stirred and heated at 75° C for 10 hours. At the end of this period the mixture was filtered hot and the catalyst was washed on the filter with two portions, each of 20 ml., of ether. The cooled filtrate and the ether washings were combined and were washed with 100 ml. of 1% w/w aqueous sodium carbonate solution followed by two 100 ml. portions of water. The ether solution was dried over anhydrous magnesium sulfate, filtered, and the filtrate was evaporated to remove ether. The residue was then worked up by distillation as described in Example 1. The solid residue remaining after removal of the phenol and resorcinol was 6 g. (52.6% conversion based on phenol consumed) of crude Bisphenol A which was found by high pressure liquid chromatography to contain 99.1 percent by weight of Bisphenol A (93.7 percent 4,4'-isomer: 6.3 percent 2,4'-isomer) and 0.4% by weight of 4-(p-hydroxyphenyl)-2,2,4-trimethylchroman and 0.5 percent by weight of higher oligomers.

EXAMPLE 5

The procedure described in Example 4 was repeated exactly as described with the exception that the amount of resorcinol was increased to 1.1 g. (10 mmol.) and the amount of thioglycolic acid was increased to 0.46 g. (5 mmol.) and the reaction was carried out at 80° C instead of 75° C. The heating period was shortened to 6 hours. There was thus obtained 6.36 g. (55.8 percent conversion based on phenol consumed) of crude Bisphenol A which was found by high pressure liquid chromatography to contain 99.4 percent by weight of Bisphenol A (95.0 percent 4,4'-isomer: 4.4 percent of 2,4'-isomer) and 0.6 percent by weight of 4-(p-hydroxyphenyl)-2,2,4-trimethylchroman.

EXAMPLE 6

The procedure described in Example 4 was repeated exactly as described except that the KSF catalyst was replaced by 6.3 g. of Amberlyst (a polystyrene polysulfonic acid; >60 mesh; Rohm & Haas Co., Philadelphia, Pa.) and the heating time was reduced to 1 hour. The product was worked up as described in Example 4 and the solid residue remaining after removal of phenol, acetone, and resorcinol was 8.95 g. (78.5 percent conversion based on phenol consumed) of crude Bisphenol A. The latter was found, by high pressure liquid chromatography, to contain 98.5 percent by weight of Bisphenol A (94.9 percent 4,4'-isomer; 5.1 percent 2,4'-isomer), 0.1 percent by weight of 4-(p-hydroxyphenyl)-2,2,4-trimethylchroman and 1.4 percent by weight of higher oligomers.

EXAMPLE 7

For purposes of comparison the process described in Example 6 was repeated but omitting the resorcinol and thioglycolic acid and maintaining the heating (at 65° C) for 25 hours. There was obtained 6.3 g. (55.3 percent conversion based on phenol consumed) of crude Bisphenol A which was found, by high pressure liquid chromatography, to contain 93.8 percent by weight of crude Bisphenol A (87.5 percent 4,4'-isomer; 12.5 percent 2,4'-isomer), 3.8 percent by weight of 4-(p-hydroxyphenyl)-2,2,4-trimethylchroman and 2.4 percent by weight of higher oligomers.

EXAMPLE 8

Also for purposes of comparison the process described in Example 6 was repeated but omitting only the resorcinol and not the thioglycolic acid. The heating was maintained at 65° C for 5.5 hours. There was obtained 7.36 g. (65 percent conversion based on phenol consumed) of crude Bisphenol A which was found, by high pressure liquid chromatography, to contain 95.4 percent by weight of Bisphenol A (92.3 percent 4,4'-isomer: 7.7 percent 2,4'-isomer), 1.2 percent by weight of 4-(p-hydroxyphenyl)-2,2,4-trimethylchroman and 3.4 percent by weight of higher oligomers.

EXAMPLE 9

The process of Example 6 was repeated exactly as described except that the thioglycolic acid was omitted, leaving only the resorcinol as cocatalyst, and the heating was maintained for 2.2 hours at 65° C. After working up the product as described in Example 6, the conversion was 75.7 percent based on phenol consumed. The crude product was found, by high pressure liquid chromatography, to contain 98 percent by weight of Bisphenol A (93.8 percent 4,4'-isomer: 6.2 percent 2,4'-isomer), 0.7 percent by weight of 4-(p-hydroxyphenyl)-2,2,4-trimethylchroman and 1.3 percent by weight of higher oligomers.

EXAMPLE 10

The process of Example 6 was repeated exactly as described except that the reaction temperature was 65° C and the heating period was extended to 1.5 hours. After working up the product as described in Example 6, there was obtained 9.53 g. (83.7 percent conversion based on phenol consumed) of the crude product which was found, by high pressure liquid chromatography, to contain 98.1 percent by weight of Bisphenol A (94.3 percent 4,4'-isomer: 5.7 percent 2,4'-isomer), 0.4 percent by weight of 4-(p-hydroxyphenyl)-2,2,4-trimethylchroman and 1.5 percent by weight of higher oligomers.

I claim:

1. In a process for the preparation of Bisphenol A by condensing phenol and acetone in the presence of acidic catalyst the improvement which comprises employing as cocatalyst, in an amount from 0.1 to 10 moles percent based on phenol, a member selected from the group consisting of compounds of the formulae:

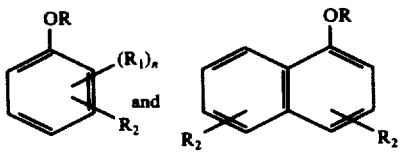

wherein R and $R_2$ are independently selected from the class consisting of hydrogen and lower-alkyl, $R_1$ is selected from the class consisting of hydroxyl, lower-alkoxy and lower-alkyl, $R_3$ is selected from the class consisting of hydrogen, hydroxyl, lower-alkoxy and lower-alkyl and $n$ is an integer from 1 to 2.

2. The process of claim 1 wherein said cocatalyst member is resorcinol.

3. The process of claim 1 wherein, in addition to said acidic catalyst and said cocatalyst member, there is also employed a catalytic amount of a thiol.

4. The process of claim 3 wherein said thiol is thioglycolic acid.

5. The process of claim 1 wherein the acidic catalyst employed in said condensation is hydrochloric acid.

6. The process of claim 1 wherein the acidic catalyst is an acid clay.

7. The process of claim 6 wherein the acid clay is an acid-treated montmorillonite clay.

8. The process of claim 1 wherein the acidic catalyst is boron trifluoride etherate.

9. The process of claim 1 wherein the acidic catalyst is a cation exchange resin.

10. The process of claim 1 wherein the acidic catalyst is a polystyrene polysulfonic acid.

11. In a process for the preparation of Bisphenol A by the condensation of acetone and phenol the improvement which comprises employing as the catalyst a combination of an acid catalyst and, as cocatalyst, from 0.1 to 10 moles percent, based on phenol, of resorcinol.

12. The process of claim 11 wherein the acid catalyst is hydrochloric acid.

13. The process of claim 11 wherein the acid catalyst is an acid clay.

14. the process of claim 13 wherein the acid clay is an acid-treated montmorillonite clay.

15. The process of claim 11 wherein the acid catalyst is boron trifluoride etherate.

16. The process of claim 11 wherein the acid catalyst is a cation ion exchange resin.

17. The process of claim 11 wherein the acid catalyst is a polystyrene polysulfonic acid.

18. The process of claim 11 wherein the catalyst combination also comprises thioglycolic acid.

19. A process for the preparation of Bisphenol A which comprises condensing acetone and phenol, said phenol being employed in excess of an amount corresponding to 2 moles of phenol per mole of acetone, at a temperture in the range of 40° to 100° C and in the presence of an acidic catalyst and, as cocatalysts, resorcinol and thioglycolic acid in amount of 0.1 to 10 moles percent based on phenol.

20. The process of claim 19 wherein the acid catalyst is hydrochloric acid.

21. The process of claim 19 wherein the acid catalyst is an acid clay.

22. The process of claim 21 wherein the acid clay is an acid-treated montmorillonite clay.

23. The process of claim 19 wherein the acid catalyst is boron trifluoride etherate.

24. The process of claim 19 wherein the acid catalyst is a cation exchange resin.

25. The process of claim 19 wherein the acid catalyst is a polystyrene polysulfonic acid.

* * * * *